US010327934B2

(12) United States Patent
Havel et al.

(10) Patent No.: US 10,327,934 B2
(45) **Date of Patent: *Jun. 25, 2019**

(54) PROSTHESIS DELIVERY DEVICE

(71) Applicant: COOK MEDICAL TECHNOLOGIES LLC, Bloomington, IN (US)

(72) Inventors: William J. Havel, West Lafayette, IN (US); Jarin A. Kratzberg, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/262,657

(22) Filed: Sep. 12, 2016

(65) Prior Publication Data

US 2016/0374842 A1 Dec. 29, 2016

Related U.S. Application Data

(63) Continuation of application No. 13/844,237, filed on Mar. 15, 2013, now Pat. No. 9,439,796.

(51) Int. Cl.
*A61F 2/966* (2013.01)
*A61F 2/962* (2013.01)
(Continued)

(52) U.S. Cl.
CPC ................ *A61F 2/966* (2013.01); *A61F 2/07* (2013.01); *A61F 2/95* (2013.01); *A61F 2/962* (2013.01);
(Continued)

(58) Field of Classification Search
CPC .. A61F 2/95; A61F 2/962; A61F 2/966; A61F 2002/9505; A61F 2002/9517; A61F 2002/9665
See application file for complete search history.

(56) References Cited

U.S. PATENT DOCUMENTS

2004/0098079 A1 5/2004 Hartley et al.
2005/0171479 A1 8/2005 Hruska et al.
(Continued)

FOREIGN PATENT DOCUMENTS

WO WO 2010/120926 A1 10/2010

OTHER PUBLICATIONS

Extended European Search Report for European Application No. 16185011.0, dated Dec. 20, 2016, 8 pages.
(Continued)

*Primary Examiner* — Robert A Lynch
(74) *Attorney, Agent, or Firm* — Brinks Gilson & Lione

(57) ABSTRACT

A prosthesis delivery device comprises a proximal end and a distal end, a prosthesis retention section at the proximal end, and a prosthesis retained on the prosthesis retention section. The prosthesis has a proximal end releasably attached at the prosthesis retention section and a distal end releasably attached at the prosthesis retention section. A sheath is slidably disposed over the prosthesis. A delivery handle near the distal end the delivery device comprises a rotatable inner cannula having a cannula lumen and cannula handle. The cannula handle is rotatable with the inner cannula. Further, a positioner handle is releasably engaged with the cannula handle. Rotation of the inner cannula releases the proximal end of the prosthesis from the delivery device and withdrawal of the sheath from over the prosthesis releases the distal end of the prosthesis from the delivery device.

15 Claims, 10 Drawing Sheets

103 100 110 116 126 112 208 200

(51) Int. Cl.
*A61F 2/95* (2013.01)
*A61F 2/07* (2013.01)

(52) U.S. Cl.
CPC ................. *A61F 2002/9505* (2013.01); *A61F 2002/9517* (2013.01); *A61F 2002/9665* (2013.01)

(56) References Cited

U.S. PATENT DOCUMENTS

| | | | |
|---|---|---|---|
| 2006/0271153 | A1 | 11/2006 | Garcia et al. |
| 2007/0078395 | A1 | 4/2007 | Valaie |
| 2008/0157017 | A1 | 7/2008 | Macatangay et al. |
| 2009/0192601 | A1 | 7/2009 | Rafiee et al. |
| 2011/0054585 | A1 | 3/2011 | Osborne |
| 2011/0251664 | A1 | 10/2011 | Acosta De Acevedo |
| 2011/0307049 | A1 | 12/2011 | Kao |
| 2012/0238958 | A1 | 9/2012 | Moore |
| 2012/0310178 | A1 | 12/2012 | Goode et al. |
| 2013/0338787 | A1 | 12/2013 | Hopkins et al. |

OTHER PUBLICATIONS

European Search Report for corresponding EP 14275065 dated Jul. 17, 2014, 6 pages.

PROSTHESIS DELIVERY DEVICE

RELATED APPLICATIONS

The present patent document is a continuation of application Ser. No. 13/844,237, filed Mar. 15, 2013, which is hereby incorporated by reference in its entirety.

TECHNICAL FIELD

This invention relates to medical device delivery systems for the introduction of a medical device into a patient, in particular to an introducer/delivery device, systems and methods for delivering a prosthesis to an implantation site in a patient.

BACKGROUND OF THE INVENTION

The present invention relates to delivery devices for prostheses, such as stents, grafts and stent grafts (collectively prostheses) in the vascular system of a patient. In particular, the invention relates to a prosthesis delivery system, device and method that provides the controlled release and implantation of a prosthesis in a controlled manner. In particular, the invention relates to an introducer/delivery device delivery handle that permits controlled release of a prosthesis from the introducer/delivery device.

BRIEF SUMMARY OF THE INVENTION

A prosthesis delivery device comprises a proximal end and a distal end, a prosthesis retention section at the proximal end, and a prosthesis retained on the prosthesis retention section. The prosthesis has a proximal end releasably attached at the prosthesis retention section and a distal end releasably attached at the prosthesis retention section. A sheath is slidably disposed over the prosthesis. A delivery handle near the distal end the delivery device comprises a rotatable inner cannula having a cannula lumen and cannula handle. The cannula handle is rotatable with the inner cannula, the inner cannula having a proximal end releasably engaged to the proximal end of the prosthesis.

Further, a positioner handle is releasably engaged with the cannula handle. Rotation of the inner cannula releases the proximal end of the prosthesis from the delivery device and withdrawal of the sheath from over the prosthesis releases the distal end of the prosthesis from the delivery device.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The accompanying drawings are included to provide a further understanding of the claims, are incorporated in, and constitute a part of this specification. The detailed description and illustrated examples described serve to explain the principles defined by the claims.

DETAILED DESCRIPTION OF THE INVENTION

Figure 1:
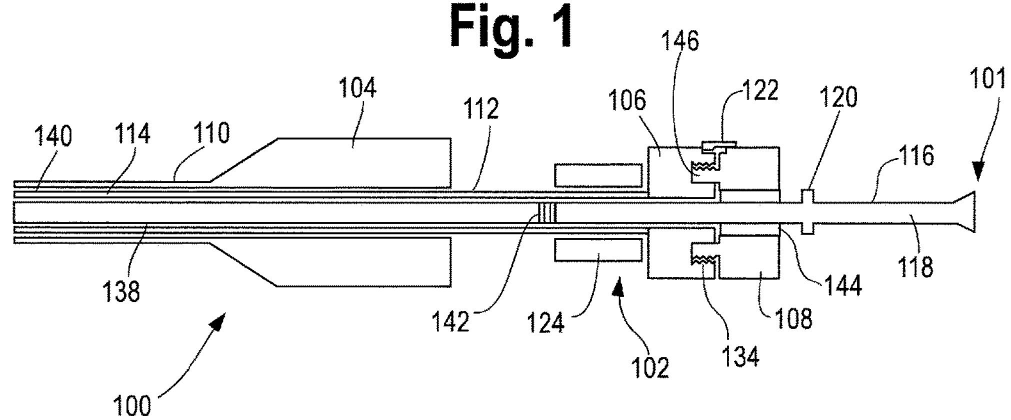
FIG. 1 is a partial side view of a prosthesis delivery device, in particular the handle portion of the device at the distal end of the delivery device.

The embodiments described in this disclosure will be discussed generally in relation to deployment of prostheses, such as stents, grafts and stent grafts into the aorta, but the disclosure is not so limited and may be applied to other vasculature or other body vessels or lumens.

In the present application, the term “proximal” refers to a direction that is generally closest to the heart during a medical procedure, while the term “distal” refers to a direction that is furthest from the heart during a medical procedure.

The term “stent graft” refers to a device that has a tubular body of biocompatible graft material and at least one stent fastened to the tubular body to define a lumen through the stent graft. The stent graft may be bifurcated and/or may include fenestrations, side arms, or the like. Other arrangements of stent grafts also are within the scope of this disclosure.

The present delivery device operates to release a prosthesis from a delivery device at an implantation site within a body vessel. In particular, the delivery device may release the proximal end of a prosthesis from retention at and/or within the delivery system. For example, the delivery device may release the proximal end, such as an end stent of a prosthesis from within a top cap holding the proximal end, such as an end stent of the prosthesis by twisting the cannula.

The delivery device may further release the distal end of the stent graft through sheath pull back. The distal end of the prosthesis may be held to the delivery device prior to release by holding the distal end to a part of the delivery device. In one example, a distal capture feature on the delivery device holds the distal end of the prosthesis. While the sheath is in place over the prosthesis the distal end remains held or captured on the delivery device. With the withdrawal of the sheath in a distal direction and past the distal capture feature, the distal end of the prosthesis is released from the delivery device. In this example, a trigger wire is not needed to retain the distal end of prosthesis or to release the distal end.

The delivery handle of the present delivery device includes one or more interlocks to prevent the physician from performing deployment steps out of sequence and from failing to perform or complete the delivery steps, which may be critical to the proper delivery of the prosthesis. The present device also provides a handle design that eliminates or reduces the need for the physician to remove his/her hands from the handle to complete delivery of the prosthesis, hence providing increased control over the device and the delivery process, which can mean the difference between a successful and a less than successful or unsuccessful procedure.

As described more fully below with regard to FIG. 1-5, the delivery device 100 has a deployment handle 102 which accomplishes the above functions. The handle has three primary grip points—a sheath handle 104, a positioner handle 106, and a cannula handle 108. The sheath handle 104 also may provide a valve housing for one or more valves for maintaining hemostasis. The sheath handle also may allow for flushing of the sheath. Exemplary valve structures that may be used as the one or more valves in the valve housing are shown in U.S. Patent/Publication Nos. 2012/0310178; 2005/0171479; 2007/0078395; 2008/0157017; 2011/0054585; and 2012/0238958 in which the descriptions and operations of the valves disclosed are incorporated by reference in their entirety herein. In operation, the sheath handle 104 is gripped by the physician to withdraw the sheath from over the prosthesis.

The second handle, the positioner handle 106, maintains the position of the prosthesis during all stages of deployment. The positioner handle 106 provides a consistent point of reference of the prosthesis during the procedure. The third handle, the cannula handle 108, provides control over the cannula and the proximal end of the delivery device. Specifically, the cannula handle 108 provides rotational control of the cannula and hence controls release of the proximal part or stent of the prosthesis from the delivery device.

FIGS. 1-5 illustrate prosthesis delivery device 100 with deployment handle 102 as it is operated by a user to release the proximal and distal ends of a prosthesis, such as a stent, graft or stent graft. FIGS. 6-10 illustrate an embodiment of the release of proximal end of the prosthesis with the deployment handle 102 of FIGS. 1-5 is operated as described below.

Figure 2:
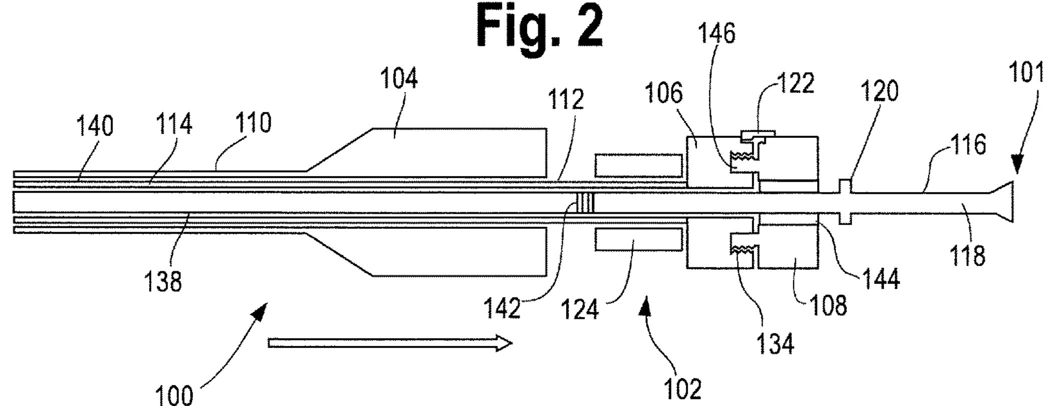
FIG. 2 is a further view of the prosthesis delivery device of FIG. 1 at a stage of deployment of a prosthesis.

FIGS. 1 and 2 show a partial side view of a prosthesis delivery device 100 having a distal end 101 a proximal end (not shown in FIGS. 1 and 2, but 103 in later figures) and a deployment handle 102 near the distal end 101 of the delivery device 100. The deployment handle 102 is intended to remain outside of the patient. As set forth above, the deployment handle 102 preferably has three primary grip points, the sheath handle 104, the positioner handle 106 and the cannula handle 108. Any or all of the handles may be provided with gripping features that provide secure and/or ergonomic gripping of the handles by the physician. Any or all of the handles may further be provided with a mechanism or ability to provide the physician with tactile feedback while gripping and/or operating the handle.

As shown in FIGS. 1-4, the deployment handle 102 includes a sheath 110, a sheath handle 104, a positioner 112 having a positioner shaft 114, a positioner handle 106, a cannula 116 having an inner lumen 118, a cannula handle 108, a cannula handle stop 120, a cannula safety 122, and a safety collar 124.

The sheath handle 104 is connected to the sheath 110. As set forth above, sheath handle 104 provides a gripping point for the physician to withdrawn the sheath from over the prosthesis for deployment. The sheath 110 extends proximally of the sheath handle 104 and is disposed over the prosthesis prior to delivery of the prosthesis to the target treatment site.

The positioner shaft 114 is operatively connected to the positioner handle 106, and extends proximally of the positioner handle 106. In a preferred embodiment, the proximal end 126 (shown in FIGS. 10-16) of the positioner handle 106 is located at or near the distal end 128 of a prosthesis 130 that is disposed on the delivery device 100. As described more fully below with reference to FIGS. 10-16, the positioner proximal end 126 may engage the distal end 128 of the prosthesis 130 by way of a releasable distal attachment and release mechanism 132. Positioner 112 further may include a positioner handle attachment region 134, for attaching to the cannula handle 108. The positioner handle attachment region 134 may be a keyed region with threading. A mechanism to limit full sheath pullback, such as safety collar 124, may be disposed on the positioner 112 and is located adjacent to the proximal end 126 of the positioner handle 106. Although safety collar 124 is shown as disposed about the shaft of the positioner, other mechanisms, such as a protrusion or other feature that at least temporarily prevents full pullback of the sheath, may be used.

The cannula 116 has a distal end 136 and a proximal end (not shown) and extends from the distal end 101 of the delivery device 100 to the proximal end 103 of the delivery device 100. The cannula 116 may have an inner lumen 118 that runs from the distal end 136 of the cannula 116 to the proximal end of the cannula and/or the delivery device 100. The cannula inner lumen 118 may accommodate a guide wire (not shown), one or more prosthesis release mechanisms (not shown), such as one or more trigger wires, and further may provide a passageway for the injection of a contrast medium through the lumen for viewing the delivery device and/or the prosthesis during a procedure.

Positioner 112 has an inner lumen 138. Cannula 116 is at least partially disposed within the inner lumen 138 of positioner 112 and, in operation, may be axially slideable and rotatable relative to the positioner 112. Sheath has sheath inner lumen 140, which lumen inner diameter may closely approximate the outer diameter of the positioner 112. Positioner 112 is at least partially disposed over the cannula 116 and may be at least partially disposed within the sheath 110 and/or the prosthesis 130.

The cannula 116 includes at least one cannula marker 142, which may be one or more marker bands, a notch, a color marker or other physical marker device that is physically viewable to the physician at least one point during the delivery procedure to indicate the completion of one or more delivery steps. Cannula 116 includes a cannula handle 108, and a cannula handle stop 120. Cannula handle 108 further may include a cannula/cannula handle connection element 144, which be keyed, and connection element 146. For example, cannula handle 108 may be keyed through the cannula/cannula handle connection element 144 to the cannula 116. The cannula/cannula handle connection element 144 permits the cannula handle 108 to slide on the cannula 116, even as the cannula handle 108 rotates the cannula 116, to the cannula handle stop 120. The cannula/cannula handle connection element 144 is more fully described with reference to FIG. 20 below. The cannula/cannula handle connection element 144 may be keyed and may include a ratchet mechanism, as known to those of skill in the art, to allow uni-directional turning. Cannula handle connection element 146, which engages the positioner handle attachment region 134, also may be keyed and is temporarily connected to the positioner handle attachment region 134. As shown in FIGS. 1 and 2, the positioner handle 106 is engaged with the cannula handle 108 through the positioner handle attachment region 134 and the cannula handle connection element 146. Although the connection between the cannula handle 116 and the positioner handle 106 is described here as a keyed connection, other connections may be contemplated or used. The cannula safety 122, which may be located on the cannula handle 108, locks the connection between the cannula handle 108 and positioner handle 106, until their disengagement is required.

As shown in the figures, cannula safety 122, which may be located on the cannula handle 108, locks the connection between the cannula handle 108 and positioner handle 106, until their disengagement is required. Cannula safety 122 prevents rotational and axial movement of the cannula handle 108 relative to the positioner handle 106 until their disengagement. The cannula safety 122 may engage the positioner handle 106 through a latching or other engagement, such as a pin, clip and others known to one of skill in the art. Further, rather than be provided on the cannula handle, the safety may be provided on the positioner handle 106.

In FIG. 2 the graft deployment handle 102 is shown with the sheath 110 partially withdrawn along the positioner 112 in the distal direction as indicated by the arrow. In operation, the physician places one hand on the sheath handle 104 (valve housing) and the second hand on the positioner handle 106, which is initially combined with the cannula handle 108. The physician slowly pulls the sheath handle in the direction of the arrow shown in FIG. 2 toward the positioner handle to unsheath the prosthesis. The positioner shaft 114 is constructed of a material or in such a manner to have sufficient rigidity/stiffness to resist buckling of the positioner shaft 114 as sheath 110 is withdrawn over it. The safety collar 124 on the positioner shaft 114 prevents the sheath handle 104 from moving too far distally and prematurely releasing the distal attachment of the prosthesis.

Figure 3:
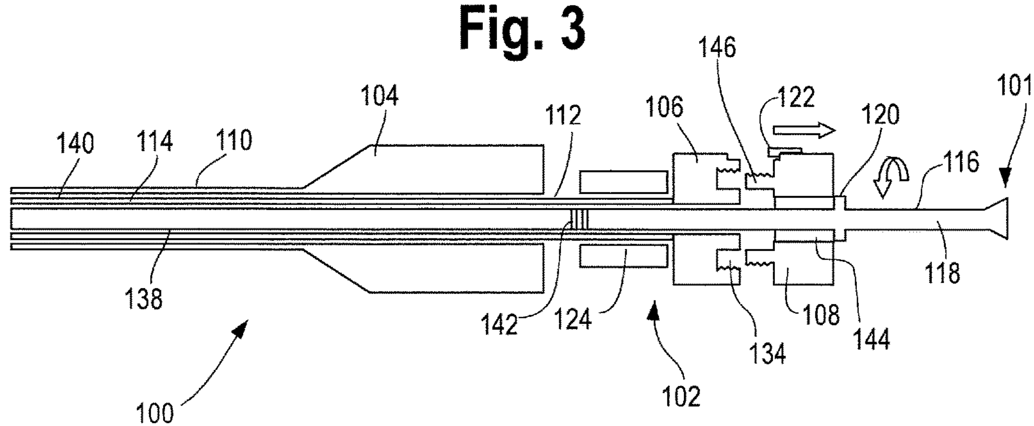
FIG. 3 is a further side view of the prosthesis delivery device of the FIG. 1 at another stage of deployment of the prosthesis.

FIG. 3 shows the deployment handle 102 with the cannula safety 122 disengaged from the positioner handle 106. The cannula safety 122 may be disengaged from the positioner handle 106 by moving the cannula safety 122 distally, as shown by the arrow in FIG. 3. The cannula handle 108 and cannula 116 are rotated as shown by the arrow in FIG. 3 to disengage the cannula handle 108 from the positioner handle 106. As set forth above, the cannula handle 108 is connected to the cannula 116 through the cannula/cannula handle connection element 144 which causes the cannula 116 to turn as the cannula handle 108 is disengaged from the positioner handle 106.

As the cannula handle 108 rotates the cannula 116, the cannula handle 108 is removed from engagement with the positioner handle 116 by, for example, unthreading the cannula handle 108 from the positioner handle 106. As the unthreading or disconnection occurs, the cannula handle 108 separates from the positioner handle 106 and slides axially along the cannula 116 in a distal direction until it reaches the cannula handle stop 120 as shown in FIG. 3. As set forth above, the cannula handle 108 includes a mechanism, such as a ratchet mechanism, to permit rotation in a single direction.

The number of turns required to separate the two handles is preferably equal to the minimum number of cannula turns required to release the proximal end of the prosthesis from its holding mechanism. Once the cannula handle 108 and the positioner handle 106 are separated, the cannula handle 108 may be further withdrawn to pull the delivery device tip out of the proximal region of the prosthesis, such as the area where one or more stents are located at the proximal end, and into the main body of the prosthesis. When the cannula handle 108 makes contact with cannula handle stop 120, further withdrawal of the handle causes pullback of the cannula 116 as shown by the arrow in FIG. 4 to a desired point. Marker(s) 142 on the cannula gives the physician the visual indication that the cannula 116 is pulled back to the desired point. In lieu of a marker, a further stop may be provided to limit the pullback of the cannula to the desired point.

Figure 5:
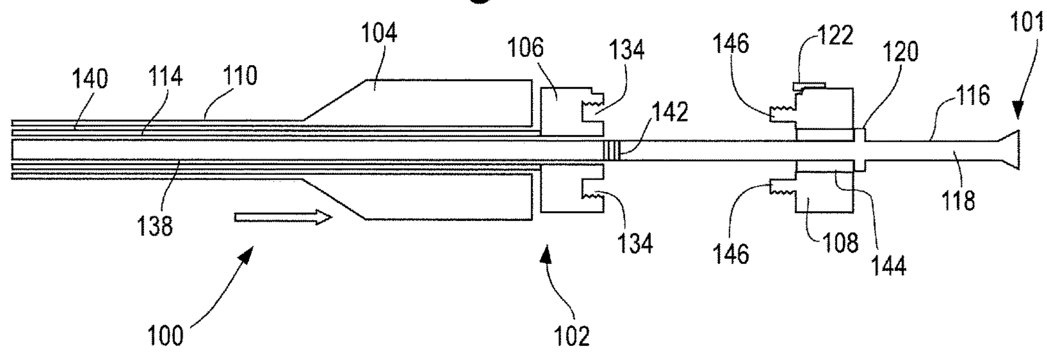
FIG. 5 is a further side view of the prosthesis delivery device of the FIG. 1 at another stage of deployment stage of deployment of the prosthesis

FIG. 5 further shows the completion of the retraction of the sheath 110. Up to this point, further retraction of the sheath 110 has been prevented by a mechanism 124 to prevent sheath pullback, such as a removable safety collar 124. As shown, the safety collar 124 is removed from the positioner shaft 114 and the sheath 110 is further withdrawn in a distal direction until the sheath 110 is adjacent to the proximal end of the positioner handle 106. The safety collar 124 may be a hinge ring that may be opened and removed from the positioner. The further withdrawal of the sheath 110 exposes the proximal end (shown in FIGS. 10-16 as element 126) of the positioner 112 and releases the distal end 128 of prosthesis 130 from the positioner 112, as discussed in further detail below.

Figure 4:
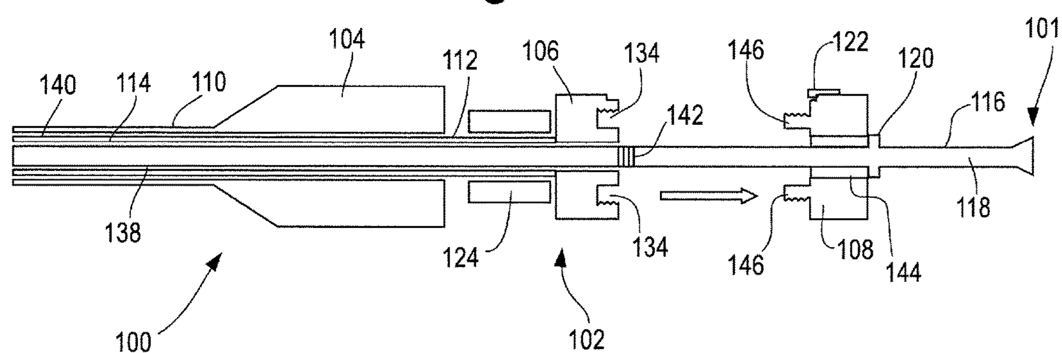
FIG. 4 is a further side view of the prosthesis delivery device of the FIG. 1 at another stage of deployment of the prosthesis

As set forth above, the various features described provide for sequential operation of the delivery device with various interlocks to prevent performing of the deployment steps in the wrong order and require completion or to prevent completion of the steps. In summary, the sheath 110 is pulled back to partially release the prosthesis from the sheath. The sheath is prevented from complete pullback due to a safety mechanism, such as a collar, that prevents further movement (FIG. 2 showing sheath handle moves in the direction of the arrow). A safety connecting the positioner handle and the cannula handle is released and the cannula handle is unthreaded from the positioner handle by rotating the cannula handle (FIG. 3). This unthreading also causes the cannula handle to move distally dues to its keyed relationship with the cannula (FIG. 3). The cannula handle moves distally until it meets the cannula stop, at which point the cannula and the cannula handle move distally together to fully disengage the cannula handle from the positioner handle (FIG. 3). The unthreading of the cannula handle from the positioner handle by rotating the cannula handle serves to rotate the proximal end of the cannula to release the proximal end of the prosthesis from the delivery device as will be explained in detail below. When the cannula handle 108 makes contact with cannula handle stop 120, further withdrawal of the handle causes pullback of the cannula 116 as shown by the arrow in FIG. 4. Marker(s) 142 on the cannula gives the physician the visual indication that the cannula 116 is pulled back to the desired point. (FIG. 4). The safety collar 124 is then removed permitting further withdrawal of the sheath over and off the prosthesis. This further withdrawal of the sheath operates to release the distal end of the prosthesis from the delivery device as further explained below.

Figure 6:
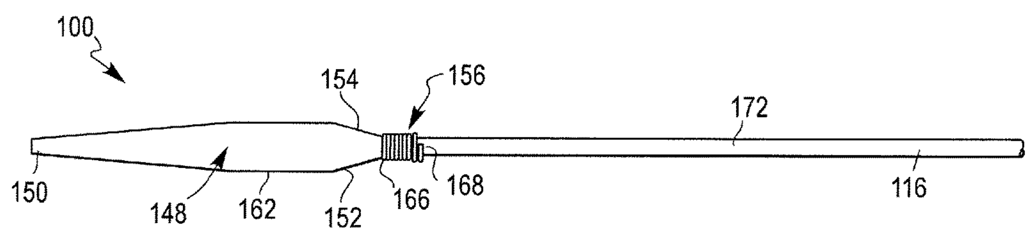
FIG. 6 is a partial side view of a proximal end of a delivery device with an exemplary prosthesis end attachment and release mechanism.
Figure 7:
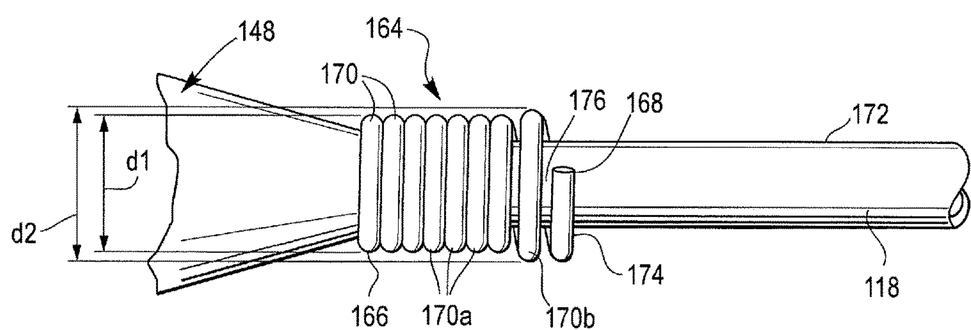
FIG. 7 is a close up partial side view of the proximal end attachment and release mechanism

FIGS. 6 and 7 show partial views of a proximal end and proximal portion of the delivery device 100, and illustrate an embodiment of a prosthesis proximal attachment and release mechanism for the release of the proximal end of the prosthesis using the delivery handle described above. FIG. 6 shows the cannula 116, a tapered nose cone/dilator 148 having a proximal tip 150. As shown, nose cone 148 has a reverse distal taper 152 at its distal end 154. The nose cone surface 162 presents a smooth tapered surface to facilitate entry into and movement through a body vessel. An exemplary prosthesis proximal end attachment and release mechanism 156 is disposed at or near the distal end 154 of the nose cone 148 and on the cannula 116. FIG. 7 shows the proximal end attachment and release mechanism 156 in greater detail. The proximal end attachment and release mechanism 156 comprises coiled member 164 which comprises a proximal end 166, a distal end 168, and a plurality of turns 170 disposed therebetween, as shown in FIG. 7. In this non-limiting example, the proximal end 166 of the coiled member 164 is secured to the outer surface 172 of the cannula 116 using a suitable mechanism, such as a solder, weld, mechanical attachment, friction fit, crimp, or combination of these or other techniques and mechanisms. Accordingly, the proximal end 166 of the coiled member 164 cannot move relative to the outer surface 172 of the cannula 116. The proximal end 166 of the coiled member 164 comprises a first diameter d1, which may be approximately the same diameter, or slightly greater than, an outer diameter of the cannula 116.

The distal end 168 of the coiled member 164 is unsecured relative to the outer surface 172 of the cannula 30, as shown. The distal end 168 of the coiled member 164 may comprise a second diameter d2, which is greater than the first diameter d1 of the proximal end 166 of the coiled member 164. There is a separation or gap 174 between the distal end 168 of the coiled member 164 and the outer surface 172 of the cannula 116, as best seen in FIG. 7.

The plurality of turns 170 are divided into a proximal series of turns 170*a*, which have the first diameter d1, and a distal series of turns 170*b*, which have the second diameter d2. The proximal series of turns 170*a* may be disposed in close proximity or abutting one another, as depicted in FIG. 7. By contrast, the distal series of turns 170*b* may be spaced apart from one another a greater distance than the proximal series of turns 170*a*. In FIG. 7, the distal series of turns 170*b* are spaced apart a predetermined distance denoted by spacing 176.

Figure 8:
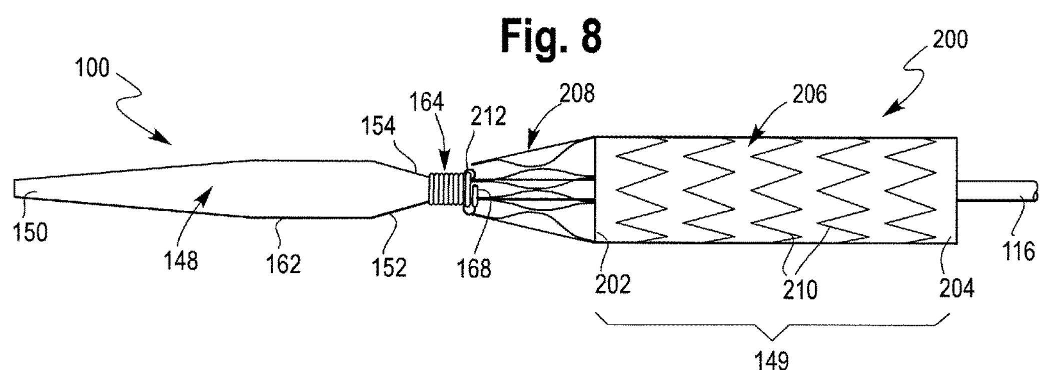
FIG. 8 shows a partial side view of the delivery device of FIG. 6 having a prosthesis on the delivery device with the proximal end stent attached to the proximal end attachment and release mechanism.
Figure 9:
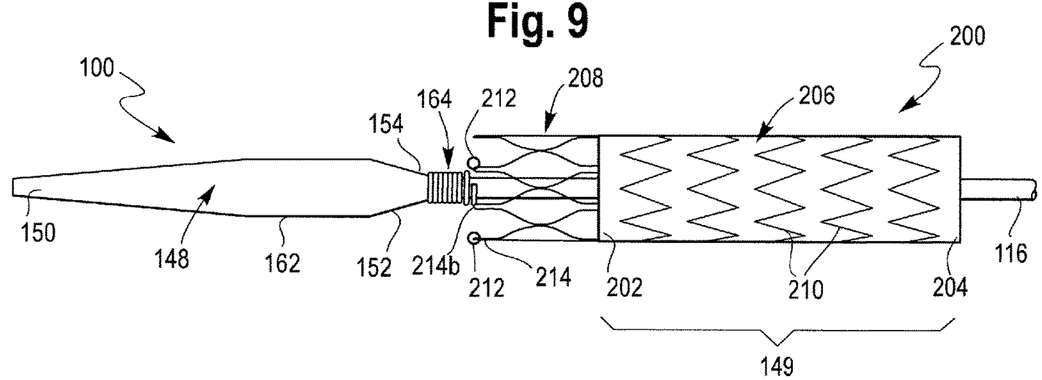
FIG. 9 shows the device of FIG. 8 with the end stent released from the proximal end attachment and release mechanism.

As shown in FIGS. 8 and 9, stent graft 200 is disposed on the device and has a proximal end 202 and distal end 204. Stent graft 200 includes, in this example, a graft material 206, a bare proximal top stent 208 (though the disclosure is not so limited), and one or more stents 210 attached to the graft material 206. The stents 210 may be on either or both surfaces of the tube of graft material 206 and may have the characteristics of self expanding stents, balloon expanding stents, or both, depending on the desired stent characteristics.

At or adjacent the distal end 154 of the nose cone 148, a proximal prosthesis retention mechanism 156 (shown in the dotted box, which is not part of the device) may be disposed. For example, the release mechanism may include the coiled member 164 discussed with regard to FIGS. 6 and 7, and further include at least one suture loop 212.

In FIGS. 8 and 9, an exemplary coupling of the stent graft 200 to the delivery device 100 of FIG. 1-5 is shown and described. The stent graft 200 has an uncoupled state in which the stent graft 200 is positioned coaxially over the cannula 116 with the proximal end 202 of the stent graft 200 in longitudinal proximity relative to the distal end 216 of the coiled member 164, as shown in FIG. 9. During assembly, one or more suture loops 212 that are coupled to the proximal apices 214 of the stent 208 are threaded around the distal end 160 of the coiled member 164 one at a time, preferably until all of the suture loops 212 are coupled to the coiled member 164. Such coupling may be achieved by rotating the cannula 116 in a clockwise direction until the proximal end 202 of the stent 208 is sufficiently compressed in a radially inward direction, as depicted in FIG. 8. As gap between the distal end 160 of the coiled member 164 and the outer surface of the cannula 116 permits positioning of the suture loops 212 in the series of turns at the distal end 160 of the coiled member 164. This type of attachment system of the proximal stent to the delivery system is more fully described with reference to FIGS. 4 and 5 of U.S. application Ser. No. 13/796,395 (filed Mar. 12, 2013) which description and Figures, and in particular FIGS. 1, 2, 4 and 5 and the corresponding description are hereby incorporated by reference in their entirety.

The suture loops 212 are further accommodated within a spacing between the distal series of turns. The suture loops 212 preferably are coupled to the coiled member 164 in a manner in which at least one suture loop 212 is positioned around at least one full turn of the distal series of turns, and preferably around at least 1.5 turns at the distal end 168 of the coiled member 164, thereby reducing the likelihood of inadvertent uncoupling of the suture loops 212 from the coiled member 164.

The coupling shown in FIG. 9 secures the stent 208 to the cannula 116 via the coiled member 164 in a manner that may subsequently facilitate insertion of the subassembly comprising the cannula 116 and the stent graft 200 into an outer sheath. As will be apparent, the outer sheath is configured to radially restrain other regions of the stent graft 200 for delivery to a target site within a patient's anatomy.

The suture loops 212 may be coupled to every other proximal apex 214 as shown in FIG. 8 to restrain the stent 208 during delivery. The suture loops 212 are not coupled to the second proximal apices 214*b*, which may comprise barbs. By restraining the alternating proximal apices 214 using the suture loops 212 coupled to the coiled member 164, the adjacent second proximal apices 214*b* also may be indirectly pulled in a radially inward direction during delivery. The configuration of the stent 208 facilitates the indirect compression of the adjacent second proximal apices 214*b*. Since only selected ones of the proximal apices are restrained during delivery, the number of suture loops 212 may be reduced. This type of attachment system of the proximal stent to the delivery system is more fully described with reference to FIGS. 4 and 5 of U.S. application Ser. No. 13/796,395 (filed Mar. 12, 2013) which description and Figures, and in particular FIGS. 1, 2, 4 and 5 and the corresponding description are hereby incorporated by reference in their entirety.

Figure 10:
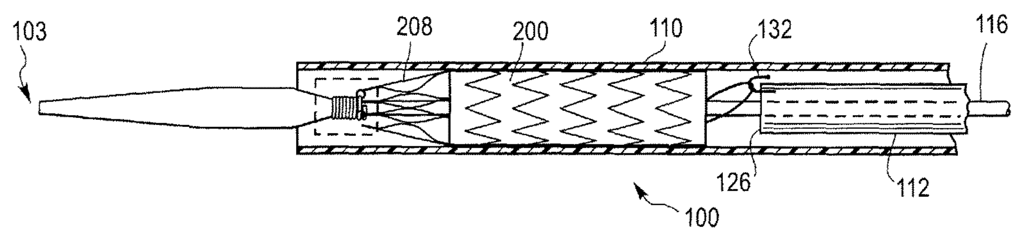
FIGS. 10-14 show further partial side views of the device of FIGS. 8 and 9 and the procedure for releasing the distal end of the prosthesis from the distal end attachment and release mechanism and releasing the proximal end of the prosthesis from the proximal end attachment and release mechanism.
Figure 15A:
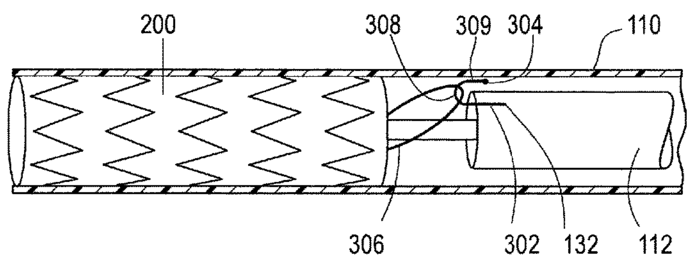
FIGS. 15A-D are perspective views of the prosthesis distal end with exemplary distal end attachment and release mechanisms.
Figure 15B:
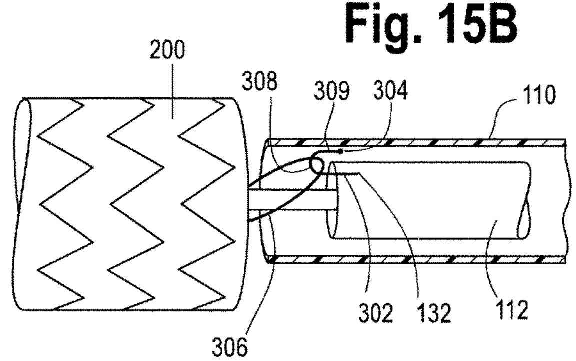
Figure 15C:
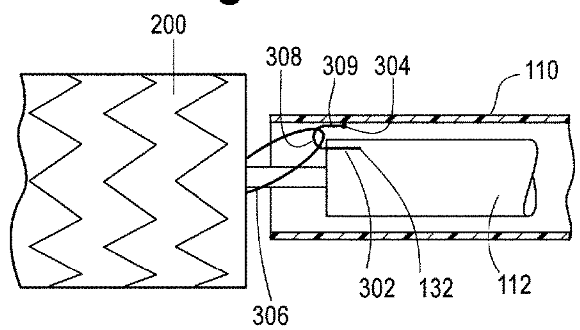
Figure 15D:
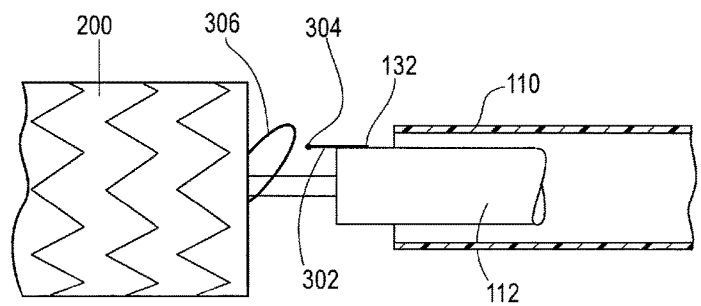
Figure 16A:
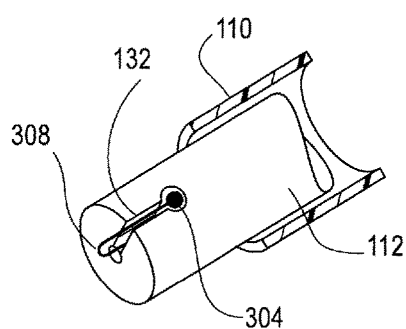
FIGS. 16A-B are perspective views of the prosthesis distal end with another exemplary distal end attachment and release mechanism.
Figure 16B:
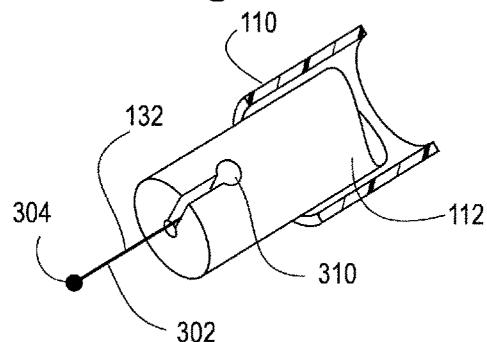

FIGS. 10-14 illustrate the release of the distal end of the stent graft, with further reference to FIGS. 15 and 16 for particular embodiments of the distal end attachment and release mechanism. FIG. 10 shows the stent graft 200 loaded on the device and compressed by the sheath 110. In operation, the operator withdraws the sheath 110 in the direction indicated by the arrow shown in FIG. 11. When the stent 208 is at least partially exposed, and it is desirable to deploy the restrained proximal end of the stent 208, the cannula 116 may be rotated in a counter-clockwise direction (as shown by the arrow in FIG. 12) until the suture loops 212 are uncoupled from the coiled member 164, i.e., in a reverse manner from which the suture loops 212 were coupled to the coiled member 164. The stent 208 then may be deployed as shown in FIGS. 8 and 9, and the remainder of the stent graft 200 may be deployed by further retraction of the sheath 110 (as shown by the arrows in FIGS. 13 and 14) or actuation of any other devices that are constraining the remainder of the stent graft 200.

Advantageously, the proximal end of the stent 208 is radially restrained without the use of conventional trigger wires that span a full longitudinal length of the delivery system. Accordingly, the radial profile of the delivery system may be reduced without the provision of multiple trigger wires and one or more associated sleeves to house the trigger wires, thereby reducing packing density of the system. Moreover, deployment may be simplified as reduced deployment forces are expected to be needed relative to the use of conventional trigger wires.

As a further advantage, deployment of a stent using the described device comprising at least one coiled member may allow for more precise positioning of the stent. In particular, deployment using the coiled member may provide a more controlled unwinding of the associated portion of the stent, whereas the release of conventional trigger wires may require higher deployment forces that can cause a portion of the stent to jump longitudinally, thereby potentially deploying the stent offset from the intended target site.

Figure 11:
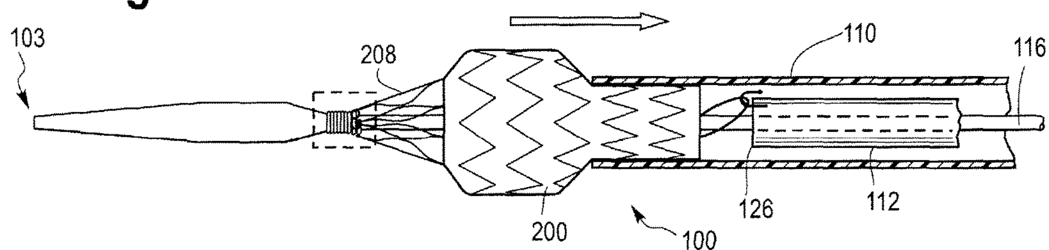
Figure 12:
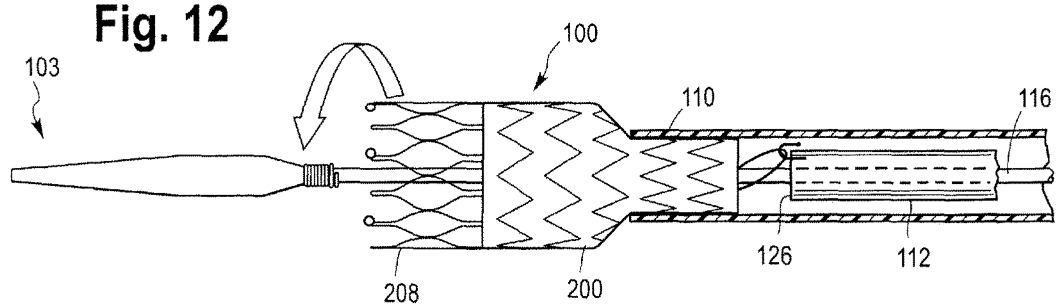
Figure 13:
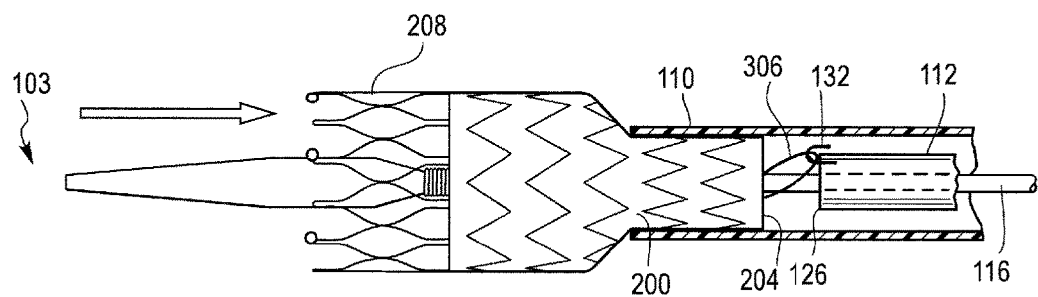
Figure 14:
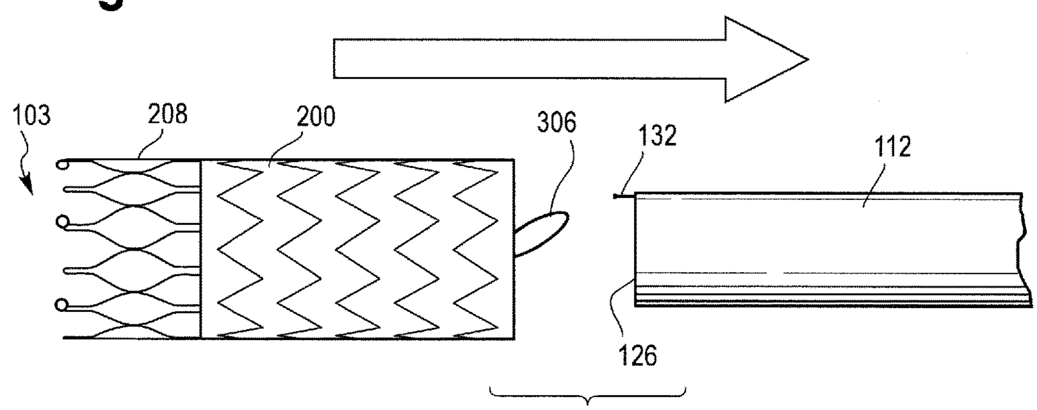

FIGS. 12-14 demonstrate the continued operation of the device to release the distal end 204 of the stent graft 200. As shown in FIGS. 10-12, the distal end 204 of the stent graft is attached to the device by way of at least one distal end capture mechanism 132 on the positioner 112 which engages a corresponding element at the distal end of the stent graft 204, such as a looped portion 306. As shown in FIG. 13, the sheath is fully withdrawn in the direction of the arrow and removed from the stent graft 200. The full withdrawal of the sheath 110 exposes the distal end 204 of the stent graft 200 and the distal end 204 of the stent graft 200 is released by releasing the loop 216 from the releasable distal attachment and release mechanism 132.

FIGS. 15A-D are perspective views of a prosthesis distal end with an exemplary distal attachment and release mechanism. In FIGS. 15A-D, the sheath 110 is shown as transparent to allow objects covered by the sheath 110 to be visible. The sheath 110 may actually be opaque or transparent. As shown, positioner 112 has releasable distal attachment and release mechanism 132 at the proximal end 126 of positioner 112. In this example, capture mechanism comprises a capture wire 302 on the positioner 112 which is bent to engage a loop 306 or other configuration at the distal end 204 of the stent graft 200. Prior to release of the distal end, the sheath 110 is over the capture wire 302. The space shown between the sheath 110, the positioner 112, and capture wire 302 in FIGS. 15A-D may be exaggerated to show the components device more clearly.

While the sheath 110 is disposed over the capture wire 302, as shown in FIGS. 15A-D, the sheath 110 prevents the bent capture wire 302 from straightening. A close fit of the sheath 110 over the positioner 112 and capture wire 302, as shown in FIG. 15B prevents the looped portion 306 from releasing or becoming detached from the capture wire 302 while the sheath is positioned over it. As shown, at least a portion of the capture wire 302 is affixed to the positioner 112. As shown, another portion 309 of the capture wire 302 may be free and not attached to positioner.

The unattached section 309 of the capture wire 302 may include an atraumatic section 304. The atraumatic section 304 may prevent damage to a vessel wall or body cavity if the unattached section 309 of the capture wire 302 contacts vessel wall or body cavity. The atraumatic section 304 may take any shape that prevents or minimizes damage to a vessel wall or body cavity that comes in contact with the atraumatic section 304, including, for example, a rounded ball, curved segment, curved end, or cushioned area.

As shown, the capture wire 302 may include one or more bends in the unattached section of the capture wire 302 when the sheath 110 covers the capture wire 302. In the case of a single bend, the bend may be approximately 180 degrees. The unattached section of the capture wire 302 is held in the bent position by the presence of the sheath 110 where the unattached section 309 is prevented from straightening out and removing the bend 308.

The capture wire 302 may be composed of any material capable of deforming and later returning to its un-deformed shape, such as bending and later straightening. The capture wire 302 may consist of, for example, nitinol or polypropylene filament. The length, thickness, and flexibility of the capture wire 302 may be varied depending on the application. For example, a thicker or less flexible capture wire 302 may be used if the looped portion 306 applies a relatively large force to the capture wire 302. A longer capture wire 302 may be used if the diameter of the looped portion 306 is relatively large or if the space between the proximal end 126 of the positioner 112 is relatively large. The capture wire 302 may return to its un-deformed or unbent shape automatically upon removal of the sheath 110 from over it. The material properties of capture wire 302 may cause it to return to an unbent or substantially straight shape without any external force applied.

FIG. 15D shows the sheath withdrawn from the capture wire 302. Removal from the sheath from over the capture wire 302 permits the capture wire 302 to be relieved from its bent shape and release loop 306 and consequently releasing the distal end 204 of the prosthesis. After the distal end is released, the device may be removed from the prosthesis and the body vessel.

Figure 17A:
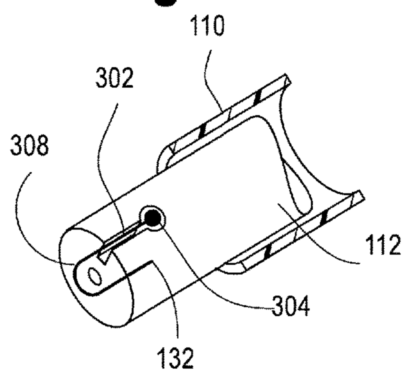
FIGS. 17A-B are perspective views of the prosthesis distal end with another exemplary distal end attachment and release mechanism.
Figure 17B:
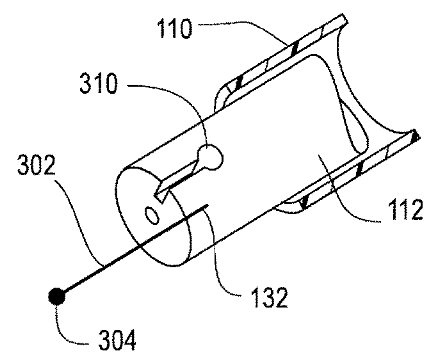
Figure 18A:
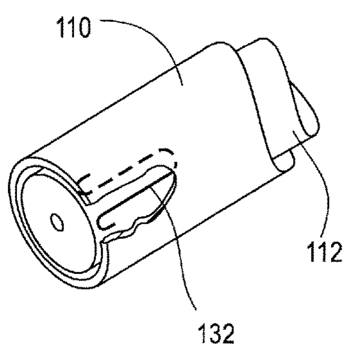
FIGS. 18A-B are perspective views of the prosthesis distal end with another exemplary distal end attachment and release mechanism.
Figure 18B:
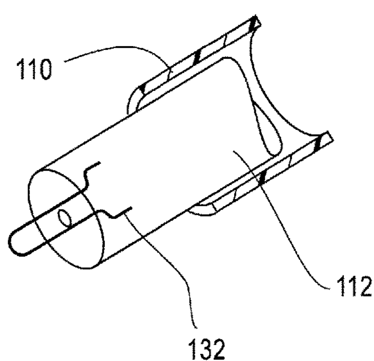

FIGS. 16-18 are further embodiments of a releasable distal attachment and release mechanism 132. The sheath 110 is shown as transparent to allow objects covered by the sheath to be visible. The sheath 110 may actually be opaque or transparent. The space shown between the sheath 110 and the positioner may be exaggerated to show the components of the exemplary medical device delivery systems more clearly, and the inner diameter of the sheath 110 may more approximate the outer diameter of the positioner 112.

As previously described with regard to FIG. 15, the capture wire 302 may include a bend 308 and an atraumatic portion 304 with the bend maintained by the presence of the sheath over the positioner 112 and the capture wire 302. In the examples of FIGS. 15 and 16, the positioner has a recessed area 310 in the surface of the positioner for receiving the capture wire 302. The recessed area 310 may contain part or all of the unattached section of capture wire 302, as shown in FIG. 16A, and may have a similar configuration to the unattached section 309, or any other shape that is capable of substantially containing the unattached section 309 of capture wire 302. Containing the unattached section 309 of capture wire 302 within the recessed area 310 may reduce the overall diameter of the delivery device, because space between the sheath and the positioner does not have to be maintained to accommodate the capture wire 302. The attached end of the capture wire 302 may attached to the positioner proximal end within the recess 310 as shown in FIG. 16 or it may be attached at another area of the surface of the positioner as shown in FIG. 17. When the capture wire 302 is bent, the free or unattached end of the capture wire 302 may be held almost entirely within the recess when the sheath is disposed over the recess as shown in FIGS. 16A and 17A. As with the capture wire 302 of FIG. 15, once the sheath 110 is withdrawn, the capture wire 302 resumes its unbent or previous shape and releases the distal end of the prosthesis.

The capture wire 302 fixed section may be attached at any location around the perimeter of the positioner proximal end, including away from the recessed area as shown in FIG. 17A. Attaching the fixed section of capture wire 302 at a location outside of the recessed area may allow the bend 308 to have a larger radius of curvature. A large radius of curvature may reduce the strain on capture wire 302 and improve is durability.

FIG. 18 shows another embodiment of the releasable distal attachment and release mechanism 132. In this embodiment the releasable distal attachment and release mechanism 132 forms a closed loop. The closed loop has two attached or fixed ends that are attached to the positioner at the proximal end. When the sheath is in place over releasable distal attachment and release mechanism 132, the loop lies against the positioner and is held there by the sheath. Although not shown, the loop engages a corresponding loop or hook at the distal end of the prosthesis. When the sheath is removed, the loop is permitted to spring away from the positioner in a proximal direction and release the distal end of the prosthesis by releasing the corresponding loop or hook. Further details regarding the embodiments of FIGS. 16-18 are set forth in the concurrently filed application entitled "Automatic Wireless Medical Device Release System," Inventors Blayne Roeder and Zach Wagner) which disclosure is incorporated in its entirety by reference herein and, in particular the disclosure regarding the capture wire.

A further embodiment of the capture mechanism is shown at FIGS. 19A-D. This embodiment and further details of its construction and use are set forth in the concurrently filed application entitled "Wireless Medical Device Release Mechanism," (Inventors William Havel, Matt Huser and Richard Hadley). As shown there, and in present FIGS. 19A-D, the proximal end of the positioner itself has a configuration that engages a portion of the distal end of the prosthesis, such as a loop as described above. As described, the engagement element 306 at the distal end of the prosthesis may be a separate loop such as a suture loop, a hook, a part of the stent, or the like.

Figure 19A:
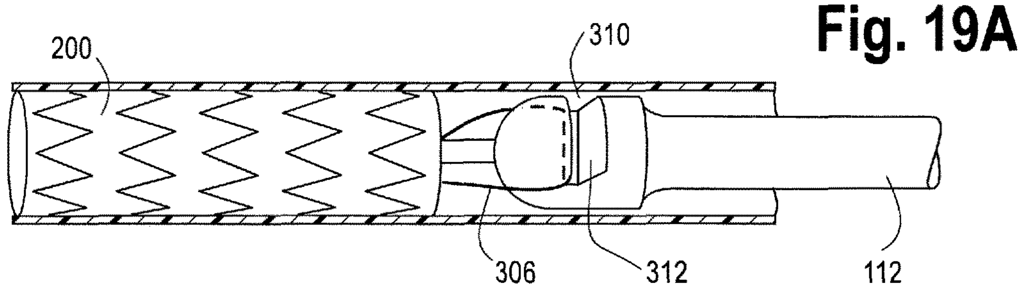
FIGS. 19A-D are perspective views of the prosthesis distal end with another exemplary distal end attachment and release mechanism.
Figure 19B:
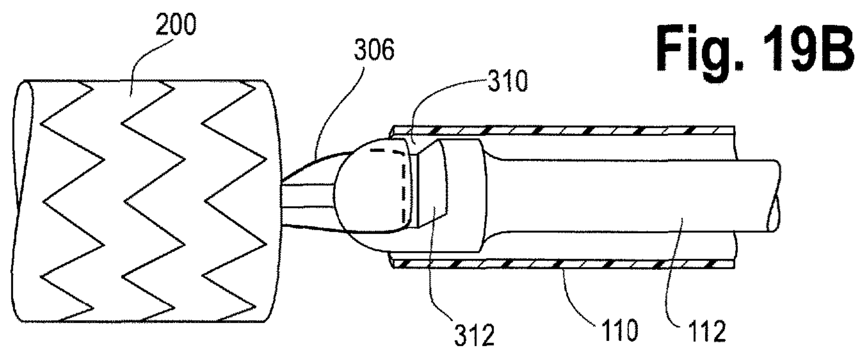
Figure 19C:
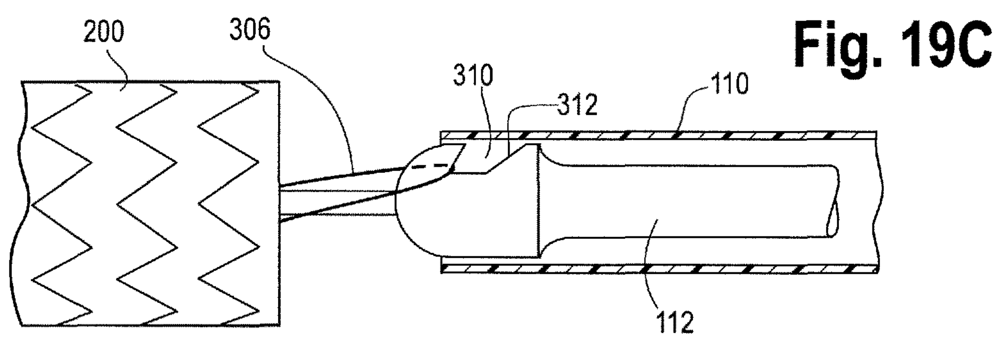
Figure 19D:
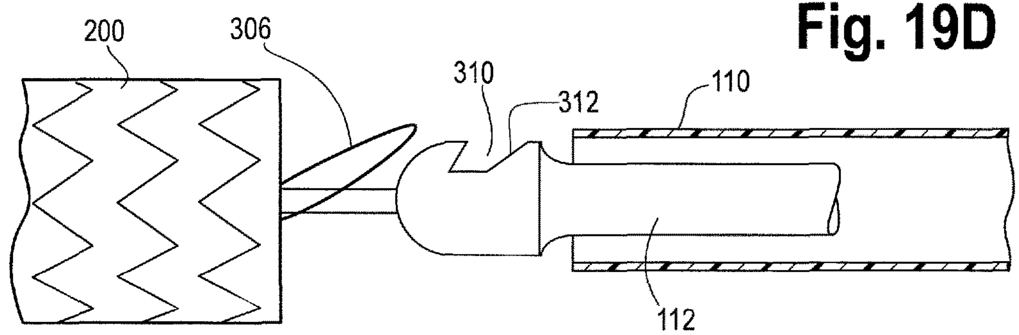

As shown in FIGS. 19A and B, the engagement element 306 of the prosthesis engages a recessed region 310 of the proximal end of the positioner 112 such that the engagement element 306 is held in the recessed region 310. For example, the engagement element 306 is held within the recess against an inclined surface 312 which may be inclined away from the prosthesis distal end, thus capturing the engagement element 306 in the recess. The recess 310 may take the form of that sent forth in FIGS. 1-16 of the concurrently filed application to Havel et al., entitled "Wireless Medical Device Release Mechanism," incorporated by reference herein, for example that shown as element 506 in FIGS. 5 and 7, and the accompanying text, of the above incorporated reference or that shown in FIGS. 8 and 9 of the incorporated reference above which includes a looped capture mechanism releasably embedded in a recess in the surface of the positioner. In the case of FIGS. 1-5 and 7, and the accompanying text, of the incorporated reference, upon removal of the sheath, a slight proximal axial movement of the positioner will release the loop from the recess and release the distal end of the prosthesis from the delivery device.

Figure 20:
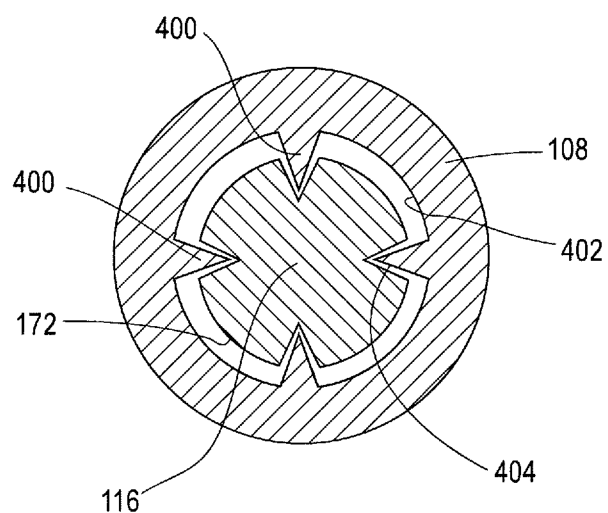
FIG. 20 is a cross-sectional view of the cannula/cannula handle connection element.

Although not so limited, FIG. 20 show an exemplary cannula/cannula connection element 144 (though not shown in this figure, cannula 116 includes a lumen as set forth above). FIG. 20 is cross-section of cannula 116 and cannula handle 108. Connection element 114 comprises one or more radially projections 400 from the inner surface 402 of the cannula handle 108 cooperating with one or more slots, channels, indents, recesses or the like 404 in cannula outer surface 172. Hence, the cannula/cannula connection element provides for rotation of the cannula with rotation of the cannula handle while also permitting longitudinal movement of the cannula handle along the cannula.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. A prosthesis delivery system comprising a delivery device having:

an introduction end configured to be introduced into a lumen of a patient during use, an operator end configured to remain outside of a patient during use, a positioner, a rotatable inner cannula having a cannula lumen, the rotatable inner cannula extending from the operator end to the introduction end, wherein the positioner is disposed at least partially over the rotatable inner cannula and the rotatable inner cannula is axially slidable and rotatable relative to the positioner, a prosthesis retention section, a prosthesis retained on the prosthesis retention section, the prosthesis having a first end disposed toward the introduction end and a second end disposed toward the operator end, a retractable sheath slidably disposed at least partially over the prosthesis, the positioner, and the inner cannula, a first end attachment and release mechanism comprising a coil disposed on the inner cannula and rotatably engaged to the first end of the prosthesis, a second end attachment and release mechanism comprising a capture wire disposed on the positioner and releasably engaged to the second end of the prosthesis, wherein rotation of the inner cannula relative to the positioner releases the first end of the prosthesis from the first end attachment and release mechanism and from the delivery device, and retraction of the sheath from over the second end attachment and release mechanism automatically releases the second end of the prosthesis from the second end attachment and release mechanism and from the delivery device.

2. The prosthesis delivery system of claim 1, wherein the prosthesis is a stent graft having an exposed stent at the first end of the stent graft.

3. The prosthesis delivery system of claim 1, wherein the exposed stent comprises apices and the coil comprises a plurality of turns about the inner cannula, wherein each of the apices of the exposed stent is disposed over at least one turn of the plurality of turns of the coil.

4. The prosthesis delivery system of claim 1, wherein the capture wire has a first end attached to the positioner, a free region, a free end, a capture position, and a release position.

5. The prosthesis delivery system of claim 4, wherein in the capture position, the capture wire has a bend in the free region.

6. The prosthesis delivery system of claim 5, wherein in the release position, the capture wire is unbent.

7. The prosthesis delivery system of claim 4, wherein the sheath maintains the capture wire in its capture position.

8. The prosthesis delivery system of claim 4, wherein the second end of the prosthesis comprises a loop and the capture wire is engaged with the loop in the capture position and is disengaged from the loop in the release position.

9. The prosthesis delivery device of claim 1, retraction of the sheath from over the second end attachment and release mechanism alone automatically and completely releases the second end of the prosthesis from the delivery device without any further mechanism or action.

10. A prosthesis delivery system comprising a delivery device having:

an introduction end configured to be introduced into a lumen of a patient during use, an operator end configured to remain outside of a patient during use, a rotatable inner cannula having a cannula lumen, the rotatable inner cannula extending from the operator end to the introduction end, a positioner disposed at least partially over the inner cannula, a prosthesis retention section, a prosthesis retained on the prosthesis retention section, the prosthesis having a first end disposed toward the introduction end and a second end disposed toward the operator end, a retractable sheath slidably disposed at least partially over the prosthesis, the positioner, and the inner cannula, a first end attachment and release mechanism comprising a coil disposed on the inner cannula and rotatably engaged to the first end of the prosthesis, a second end attachment and release mechanism comprising a capture wire disposed on the positioner and releasably engaged to the second end of the prosthesis, wherein rotation of the inner cannula relative to the positioner releases the first end of the prosthesis from the first end attachment and release mechanism and from the delivery device, and retraction of the sheath from over the second end attachment and release mechanism automatically releases the second end of the prosthesis from the second end attachment and release mechanism and from the delivery device, wherein the capture wire has first end attached to the positioner, a free region, a free end, a capture position, and a release position, and wherein the positioner comprises a recess in an outer surface of the positioner configured to receive the free end of the capture wire in the capture position.

11. A prosthesis delivery system comprising a delivery device having:

an introduction end configured to be introduced into a lumen of a patient during use, an operator end configured to remain outside of a patient during use, a rotatable inner cannula having a cannula lumen, the rotatable inner cannula extending from the operator end to the introduction end, a positioner disposed at least partially over the inner cannula, a prosthesis retention section, a prosthesis retained on the prosthesis retention section, the prosthesis having a first end disposed toward the introduction end and a second end disposed toward the operator end, a retractable sheath slidably disposed at least partially over the prosthesis, the positioner, and the inner cannula, a first end attachment and release mechanism comprising a coil disposed on the inner cannula and rotatably engaged to the first end of the prosthesis, a second end attachment and release mechanism comprising a capture wire disposed on the positioner and releasably engaged to the second end of the prosthesis, wherein rotation of the inner cannula relative to the positioner releases the first end of the prosthesis from the first end attachment and release mechanism and from the delivery device, and retraction of the sheath from over the second end attachment and release mechanism automatically releases the second end of the prosthesis from the second end attachment and release mechanism and from the delivery device, wherein the capture wire has a first end attached to the positioner, a free end, a capture position, and a release position and when in the capture position, the capture wire is disposed at least partially over the positioner and in the release position the capture wire is disposed away from the positioner and toward the first end of the delivery device.

12. A prosthesis delivery system comprising a delivery device having:

an introduction end configured to be introduced into a lumen of a patient during use, an operator end configured to remain outside of a patient during use, a positioner, a rotatable inner cannula having a cannula lumen, the rotatable inner cannula extending from the operator end to the introduction end, wherein the positioner is disposed at least partially over the rotatable inner cannula and the rotatable inner cannula is axially slideable and rotatable relative to the positioner, a prosthesis retention section, a prosthesis retained on the prosthesis retention section, the prosthesis having a first end disposed toward the introduction end and a second end disposed toward the operator end, a retractable sheath slidably disposed at least partially over the prosthesis, the positioner, and the inner cannula, a first end attachment and release mechanism disposed on the inner cannula and rotatably engaged to the first end of the prosthesis, a second end attachment and release mechanism different from and independently operable from the first end attachment and release mechanism, disposed on the positioner and releasably engaged to the second end of the prosthesis, wherein rotation of the inner cannula relative to the positioner rotates the first end attachment and release mechanism to release the first end of the prosthesis from the first end attachment and release mechanism and from the delivery device, and wherein movement of the positioner relative to sheath exposes the second attachment and release mechanism and automatically releases the second end of the prosthesis from the second end attachment and release mechanism and from the delivery device.

13. The prosthesis delivery device of claim 12, wherein the second end of the prosthesis comprises a loop and the second attachment and release mechanism is engaged with the loop.

14. The prosthesis delivery device of claim 13, wherein the second attachment and release mechanism comprises an angled notch in the positioner and the angle of the notch is engaged with the loop.

15. The prosthesis delivery device of claim 12, wherein relative movement of the sheath relative to the positioner alone automatically and completely releases the second end of the prosthesis from the delivery device without any further mechanism or action.

* * * * *